US007727168B2

(12) United States Patent
Douglas et al.

(10) Patent No.: US 7,727,168 B2
(45) Date of Patent: Jun. 1, 2010

(54) METHODS AND APPARATUS FOR SAMPLING AND ANALYZING BODY FLUID

(75) Inventors: Joel S. Douglas, Groton, CT (US);
Jeffrey N. Roe, San Ramon, CA (US);
Ryszard Radwanski, Lublin (PL);
Brent G. Duchon, Cypress, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/765,045

(22) Filed: Jun. 19, 2007

(65) Prior Publication Data
US 2007/0293747 A1 Dec. 20, 2007

Related U.S. Application Data

(60) Division of application No. 10/612,852, filed on Jul. 3, 2003, now Pat. No. 7,247,144, which is a continuation of application No. 09/887,574, filed on Jun. 21, 2001, now abandoned, which is a continuation of application No. 09/552,243, filed on Apr. 19, 2000, now Pat. No. 6,352,514, which is a continuation of application No. 09/298,386, filed on Apr. 23, 1999, now Pat. No. 6,099,484, which is a continuation of application No. 08/858,042, filed on May 16, 1997, now Pat. No. 5,951,492.

(60) Provisional application No. 60/044,406, filed on Oct. 8, 1996, provisional application No. 60/064,856, filed on Sep. 17, 1996, provisional application No. 60/092,121, filed on Sep. 16, 1996, provisional application No. 60/025,340, filed on Sep. 3, 1996, provisional application No. 60/023,658, filed on Aug. 1, 1996, provisional application No. 60/019,918, filed on Jun. 14, 1996, provisional application No. 60/017,133, filed on May 17, 1996.

(51) Int. Cl.
*A61B 5/00* (2006.01)
*B65D 81/00* (2006.01)
*A61B 17/14* (2006.01)
*A61B 17/32* (2006.01)

(52) U.S. Cl. .................. 600/583; 600/573; 600/576; 600/584; 606/181; 606/182

(58) Field of Classification Search .............. 600/573, 600/576, 583, 584; 606/181, 182
See application file for complete search history.

(56) References Cited

U.S. PATENT DOCUMENTS 720,906 A  2/1903  Eilrich et al.

(Continued)

FOREIGN PATENT DOCUMENTS

DE        34 26 090 A1     4/1985

(Continued)

OTHER PUBLICATIONS

Ash et al., "A Subcutaneous Capillary Filtrate Collector for Measurement of Blood Glucose", ASAIO Journal, 1992, vol./Issue No. 38 (3), pp. M416-M420, j.B. Lipincott Co.

(Continued)

*Primary Examiner*—Max Hindenburg
*Assistant Examiner*—Jeffrey G Hoekstra
(74) *Attorney, Agent, or Firm*—Woodard, Emhardt, Moriarty, McNett & Henry LLP (57) ABSTRACT

A sampling device for sampling body fluid includes a lancet for making an incision, a capillary tube for drawing-up body fluid from the incision, and a test strip affixed to an upper end of the capillary tube for receiving the fluid. An absorbent pad can be disposed between the test strip and capillary tube for spreading-out the fluid being transferred to the test strip. An on-site analyzer such as an optical analyzer and/or an electrochemical analyzer can be mounted in the device for analyzing the fluid. Alternatively, a test strip can be slid through a slot formed in the bottom end of the device so that by passing the device against the skin after an incision has been formed, the test strip will directly contact body fluid emanating from the incision.

17 Claims, 3 Drawing Sheets

U.S. PATENT DOCUMENTS

| | | |
|---|---|---|
| 1,960,889 A | 5/1934 | Benedict |
| 2,594,621 A | 4/1952 | Derrick |
| 2,646,799 A | 7/1953 | Jacoby |
| 2,714,890 A | 8/1955 | Vang |
| 3,030,959 A | 4/1962 | Grunert |
| 3,040,744 A | 6/1962 | Hoggard |
| 3,068,868 A | 12/1962 | Skopyk |
| 3,086,288 A | 4/1963 | Balamuth et al. |
| 3,358,689 A | 6/1964 | Higgins |
| 3,206,452 A | 9/1965 | Stern |
| 3,221,739 A | 12/1965 | Rosenthal |
| 3,486,504 A | 12/1969 | Austin |
| 3,623,475 A | 11/1971 | Sanz |
| 3,626,929 A | 12/1971 | Sanz et al. |
| 3,640,267 A | 2/1972 | Hurtig et al. |
| 3,673,475 A | 6/1972 | Britton, Jr. |
| 3,685,509 A | 8/1972 | Bentall |
| 3,734,085 A | 3/1973 | Russell |
| 3,741,197 A | 6/1973 | Sanz et al. |
| 3,774,611 A | 11/1973 | Tussey et al. |
| 3,832,776 A | 9/1974 | Sawyer |
| D238,710 S | 2/1975 | Cacanindin |
| 3,933,439 A | 1/1976 | McDonald |
| 3,964,482 A | 6/1976 | Gerstel et al. |
| 4,077,406 A | 3/1978 | Sandhage et al. |
| 4,151,832 A | 5/1979 | Hamer |
| 4,154,228 A | 5/1979 | Feldstein et al. |
| D254,444 S | 3/1980 | Levine |
| 4,203,446 A | 5/1980 | Hofert et al. |
| 4,222,380 A | 9/1980 | Terayama |
| 4,223,674 A | 9/1980 | Fluent et al. |
| 4,230,118 A | 10/1980 | Holman et al. |
| 4,235,234 A | 11/1980 | Whitney et al. |
| 4,356,826 A | 11/1982 | Kubota |
| 4,360,016 A | 11/1982 | Sarrine |
| 4,368,738 A | 1/1983 | Tersteegen et al. |
| 4,375,815 A | 3/1983 | Burns |
| 4,383,530 A | 5/1983 | Bruno |
| 4,397,643 A | 8/1983 | Rygiel |
| 4,441,510 A | 4/1984 | Worley, deceased et al. |
| 4,449,529 A | 5/1984 | Burns et al. |
| 4,460,354 A | 7/1984 | Weilbacher et al. |
| 4,462,405 A | 7/1984 | Erhlich |
| 4,469,110 A | 9/1984 | Slama |
| 4,503,856 A | 3/1985 | Cornell et al. |
| 4,517,978 A | 5/1985 | Levin et al. |
| 4,518,384 A | 5/1985 | Tarello et al. |
| 4,535,773 A | 8/1985 | Yoon |
| 4,553,541 A | 11/1985 | Burns et al. |
| 4,562,842 A | 1/1986 | Morfeld et al. |
| 4,564,513 A | 1/1986 | Becher et al. |
| 4,577,630 A | 3/1986 | Nitzsche et al. |
| 4,580,564 A | 4/1986 | Andersen |
| 4,622,974 A | 11/1986 | Coleman et al. |
| 4,627,445 A | 12/1986 | Garcia et al. |
| 4,637,403 A | 1/1987 | Garcia et al. |
| 4,637,978 A | 1/1987 | Dappen |
| 4,648,408 A | 3/1987 | Hutcheson et al. |
| 4,653,511 A | 3/1987 | Goch |
| 4,653,513 A | 3/1987 | Dombrowski |
| 4,658,821 A | 4/1987 | Chiodo et al. |
| 4,658,832 A | 4/1987 | Chiodo et al. |
| 4,660,570 A | 4/1987 | Dombrowski |
| 4,677,979 A | 7/1987 | Burns |
| 4,685,463 A | 8/1987 | Williams |
| 4,687,000 A | 8/1987 | Eisenhardt et al. |
| 4,750,489 A | 6/1988 | Berkman et al. |
| 4,772,264 A | 9/1988 | Cragg |
| 4,787,398 A | 11/1988 | Garcia et al. |
| 4,790,979 A | 12/1988 | Terminiello et al. |
| 4,794,926 A | 1/1989 | Munsch et al. |
| 4,805,623 A | 2/1989 | Jobsis |
| 4,823,806 A | 4/1989 | Bajada |
| RE32,922 E | 5/1989 | Levin et al. |
| 4,837,049 A | 6/1989 | Byers et al. |
| 4,844,095 A | 7/1989 | Chiodo et al. |
| 4,850,973 A | 7/1989 | Jordan et al. |
| 4,858,607 A | 8/1989 | Jordan et al. |
| 4,869,249 A | 9/1989 | Crossman et al. |
| 4,873,993 A | 10/1989 | Meserol et al. |
| 4,883,068 A | 11/1989 | Dechow |
| D305,065 S | 12/1989 | Büchel et al. |
| 4,895,147 A | 1/1990 | Bodicky et al. |
| 4,920,977 A | 5/1990 | Haynes |
| 4,924,879 A | 5/1990 | O'Brien |
| 4,925,447 A | 5/1990 | Rosenblatt |
| 4,953,552 A | 9/1990 | DeMarzo |
| 4,976,724 A | 12/1990 | Nieto et al. |
| 4,981,473 A | 1/1991 | Rosenblatt |
| 4,983,178 A | 1/1991 | Schnell |
| 4,990,154 A | 2/1991 | Brown et al. |
| 4,994,068 A | 2/1991 | Hufnagle |
| 4,994,073 A | 2/1991 | Green |
| 4,994,079 A | 2/1991 | Genese et al. |
| 4,995,402 A | 2/1991 | Smith et al. |
| 5,002,054 A | 3/1991 | Ash et al. |
| 5,014,718 A | 5/1991 | Mitchen |
| 5,019,059 A | 5/1991 | Goldberg et al. |
| 5,029,583 A | 7/1991 | Meserol et al. |
| 5,035,704 A | 7/1991 | Lambert et al. |
| 5,047,044 A | 9/1991 | Smith et al. |
| 5,052,403 A | 10/1991 | Haber et al. |
| 5,054,499 A | 10/1991 | Swierczek |
| 5,066,859 A | 11/1991 | Karkar et al. |
| 5,070,884 A | 12/1991 | Columbus et al. |
| 5,070,886 A | 12/1991 | Mitchen et al. |
| D324,423 S | 3/1992 | Ahlstrand et al. |
| 5,097,810 A | 3/1992 | Fishman et al. |
| 5,100,620 A | 3/1992 | Brenneman |
| 5,102,404 A | 4/1992 | Goldberg et al. |
| 5,108,889 A | 4/1992 | Smith |
| 5,145,565 A | 9/1992 | Kater et al. |
| 5,152,775 A | 10/1992 | Ruppert |
| 5,163,442 A | 11/1992 | Ono |
| 5,165,418 A | 11/1992 | Tankovich |
| D332,306 S | 1/1993 | Garth et al. |
| 5,188,118 A | 2/1993 | Terwilliger |
| 5,189,751 A | 3/1993 | Giuliani et al. |
| 5,193,552 A | 3/1993 | Columbus et al. |
| 5,195,534 A | 3/1993 | Sarrine |
| 5,201,324 A | 4/1993 | Swierczek |
| 5,212,879 A | 5/1993 | Biro et al. |
| 5,217,480 A | 6/1993 | Haber et al. |
| 5,222,504 A | 6/1993 | Solomon |
| 5,231,993 A | 8/1993 | Haber et al. |
| 5,269,800 A | 12/1993 | Davis, Jr. |
| 5,271,385 A | 12/1993 | Bailey |
| 5,277,198 A | 1/1994 | Kanner et al. |
| 5,279,294 A | 1/1994 | Anderson et al. |
| 5,279,586 A | 1/1994 | Balkwill |
| 5,282,822 A | 2/1994 | Macors et al. |
| 5,290,420 A | 3/1994 | Matson |
| 5,304,193 A | 4/1994 | Zhadanov |
| 5,309,924 A | 5/1994 | Peabody |
| 5,314,441 A | 5/1994 | Cusack et al. |
| 5,314,442 A | 5/1994 | Morita |
| 5,318,583 A | 6/1994 | Rabenau et al. |
| 5,318,584 A | 6/1994 | Lange et al. |
| 5,320,607 A | 6/1994 | Ishibashi |
| 5,320,808 A | 6/1994 | Holen et al. |
| 5,324,302 A | 6/1994 | Crouse |
| 5,324,303 A | 6/1994 | Strong et al. |
| 5,353,806 A | 10/1994 | Heinzelman et al. |
| 5,366,470 A | 11/1994 | Ramel |

| | | | | | |
|---|---|---|---|---|---|
| 5,368,047 A | 11/1994 | Suzuki et al. | 5,830,219 A | 11/1998 | Bird et al. |
| 5,387,203 A | 2/1995 | Goodrich | 5,846,490 A | 12/1998 | Yokota et al. |
| 5,395,387 A | 3/1995 | Burns | 5,851,215 A | 12/1998 | Mawhirt et al. |
| 5,402,798 A | 4/1995 | Swierczek et al. | 5,854,074 A | 12/1998 | Charlton et al. |
| 5,415,169 A | 5/1995 | Siczek et al. | 5,855,801 A | 1/1999 | Lin et al. |
| 5,421,816 A | 6/1995 | Lipkovker | 5,857,983 A | 1/1999 | Douglas et al. |
| 5,423,758 A | 6/1995 | Shaw | 5,863,800 A | 1/1999 | Eikmeier et al. |
| 5,423,847 A | 6/1995 | Strong et al. | 5,871,494 A | 2/1999 | Simons et al. |
| 5,437,640 A | 8/1995 | Schwab | 5,873,887 A | 2/1999 | King et al. |
| 5,439,473 A | 8/1995 | Jorgensen | 5,879,311 A | 3/1999 | Duchon et al. |
| 5,445,611 A | 8/1995 | Eppstein et al. | 5,879,367 A | 3/1999 | Latterell et al. |
| 5,456,875 A | 10/1995 | Lambert | 5,880,829 A | 3/1999 | Kauhaniemi et al. |
| 5,458,140 A | 10/1995 | Eppstein et al. | 5,885,211 A | 3/1999 | Eppstein et al. |
| 5,472,427 A | 12/1995 | Rammler | 5,885,219 A | 3/1999 | Nightengale |
| 5,474,084 A | 12/1995 | Cunniff | 5,891,053 A | 4/1999 | Sesekura |
| 5,476,474 A | 12/1995 | Davis et al. | 5,902,279 A | 5/1999 | Powles et al. |
| 5,487,748 A | 1/1996 | Marshall et al. | 5,916,222 A | 6/1999 | Iwasaki et al. |
| 3,235,337 A | 2/1996 | Artis | 5,916,229 A | 6/1999 | Evans |
| 5,510,266 A | 4/1996 | Bonner et al. | 5,916,230 A | 6/1999 | Brenneman et al. |
| 5,512,158 A | 4/1996 | Cole | 5,935,075 A | 8/1999 | Casscells et al. |
| 5,514,152 A | 5/1996 | Smith | 5,935,864 A | 8/1999 | Schramm et al. |
| 5,518,006 A | 5/1996 | Mawhirt et al. | 5,938,679 A | 8/1999 | Freeman et al. |
| 5,529,074 A | 6/1996 | Greenfield | 5,947,957 A | 9/1999 | Morris |
| 5,529,581 A | 6/1996 | Cusack | 5,948,695 A | 9/1999 | Douglas et al. |
| D371,440 S | 7/1996 | Petersen | 5,951,492 A | 9/1999 | Douglas et al. |
| 5,540,709 A | 7/1996 | Ramel | 5,951,493 A | 9/1999 | Douglas et al. |
| 5,545,173 A | 8/1996 | Herbst | 5,951,582 A | 9/1999 | Thorne et al. |
| 5,545,174 A | 8/1996 | Schenk et al. | 5,964,718 A | 10/1999 | Duchon et al. |
| 5,549,584 A | 8/1996 | Gross | 5,968,063 A | 10/1999 | Chu et al. |
| 5,554,166 A | 9/1996 | Lange et al. | 5,971,941 A | 10/1999 | Simons et al. |
| 5,569,212 A | 10/1996 | Brown | 5,984,940 A | 11/1999 | Davis et al. |
| 5,575,403 A | 11/1996 | Charlton et al. | 5,997,561 A | 12/1999 | Bocker et al. |
| 5,582,184 A | 12/1996 | Erickson et al. | 6,015,392 A | 1/2000 | Douglas et al. |
| 5,591,139 A | 1/1997 | Lin et al. | 6,022,324 A | 2/2000 | Skinner |
| D378,612 S | 3/1997 | Clark et al. | 6,022,366 A | 2/2000 | Schraga |
| 5,607,401 A | 3/1997 | Humphrey | 6,027,459 A | 2/2000 | Shain et al. |
| 5,611,809 A | 3/1997 | Marshall et al. | 6,036,924 A | 3/2000 | Simons et al. |
| 5,613,978 A | 3/1997 | Harding | 6,045,567 A | 4/2000 | Taylor et al. |
| 5,624,458 A | 4/1997 | Lipscher | 6,048,352 A | 4/2000 | Douglas et al. |
| 5,628,309 A | 5/1997 | Brown | 6,056,701 A | 5/2000 | Duchon et al. |
| 5,628,764 A | 5/1997 | Schraga | 6,056,765 A | 5/2000 | Bajaj et al. |
| 5,628,765 A | 5/1997 | Morita | 6,063,039 A | 5/2000 | Cunningham et al. |
| 5,630,986 A | 5/1997 | Charlton et al. | 6,066,103 A | 5/2000 | Duchon et al. |
| 5,632,410 A | 5/1997 | Moulton et al. | 6,068,599 A | 5/2000 | Saito et al. |
| 5,636,640 A | 6/1997 | Staehlin | 6,071,249 A | 6/2000 | Cunningham et al. |
| 5,638,828 A | 6/1997 | Lauks et al. | 6,071,250 A | 6/2000 | Douglas et al. |
| 5,662,127 A | 9/1997 | De Vaughn | 6,071,251 A | 6/2000 | Cunningham et al. |
| 5,666,966 A | 9/1997 | Horie et al. | 6,071,294 A | 6/2000 | Simons et al. |
| 5,671,753 A | 9/1997 | Pitesky | 6,080,116 A | 6/2000 | Erickson et al. |
| 5,680,872 A | 10/1997 | Sesekura et al. | 6,086,545 A | 7/2000 | Roe et al. |
| 5,682,233 A | 10/1997 | Brinda | 6,090,078 A | 7/2000 | Erskine |
| 5,700,695 A | 12/1997 | Yassinzadeh et al. | 6,093,156 A | 7/2000 | Cunningham et al. |
| 5,707,384 A | 1/1998 | Kim | 6,099,484 A | 8/2000 | Douglas et al. |
| 5,709,699 A | 1/1998 | Warner | 6,117,630 A | 9/2000 | Reber et al. |
| 5,714,390 A | 2/1998 | Hallowitz et al. | 6,120,462 A | 9/2000 | Hibner et al. |
| 5,720,924 A | 2/1998 | Eikmeier et al. | 6,120,676 A | 9/2000 | Heller et al. |
| 5,730,357 A | 3/1998 | Besenschek et al. | 6,132,449 A | 10/2000 | Lum et al. |
| 5,730,753 A | 3/1998 | Morita | 6,136,013 A | 10/2000 | Marshall et al. |
| 5,738,244 A | 4/1998 | Charlton et al. | 6,139,562 A | 10/2000 | Mauze et al. |
| 5,741,291 A | 4/1998 | Yoo | 6,143,164 A | 11/2000 | Heller et al. |
| RE35,803 E | 5/1998 | Lange et al. | 6,146,361 A | 11/2000 | DiBiasi et al. |
| 5,746,217 A | 5/1998 | Erickson et al. | 6,152,889 A | 11/2000 | Sopp et al. |
| 5,755,733 A | 5/1998 | Morita | 6,152,942 A | 11/2000 | Brenneman et al. |
| 5,757,666 A | 5/1998 | Schreiber et al. | 6,155,992 A | 12/2000 | Henning et al. |
| 5,758,643 A | 6/1998 | Wong et al. | 6,156,050 A | 12/2000 | Davis et al. |
| 5,776,157 A | 7/1998 | Thorne et al. | 6,156,051 A | 12/2000 | Schraga |
| 5,788,651 A | 8/1998 | Weilandt | 6,159,424 A | 12/2000 | Kauhaniemi et al. |
| 5,788,652 A | 8/1998 | Rahn | 6,162,639 A | 12/2000 | Douglas |
| 5,800,781 A | 9/1998 | Gavin et al. | 6,171,325 B1 | 1/2001 | Mauze et al. |
| 5,801,057 A | 9/1998 | Smart et al. | 6,176,865 B1 | 1/2001 | Mauze et al. |
| 5,810,199 A | 9/1998 | Charlton et al. | 6,183,434 B1 | 2/2001 | Eppstein |
| 5,820,570 A | 10/1998 | Erickson et al. | 6,183,489 B1 | 2/2001 | Douglas et al. |
| 5,823,973 A | 10/1998 | Racchini et al. | 6,193,673 B1 | 2/2001 | Viola et al. |

| | | |
|---|---|---|
| 6,203,504 B1 | 3/2001 | Latterell et al. |
| 6,206,841 B1 | 3/2001 | Cunningham et al. |
| 6,210,420 B1 | 4/2001 | Mauze et al. |
| 6,210,421 B1 | 4/2001 | Bocker et al. |
| 6,228,100 B1 | 5/2001 | Schraga |
| 6,231,531 B1 | 5/2001 | Lum et al. |
| 6,261,241 B1 | 7/2001 | Burbank et al. |
| 6,261,244 B1 | 7/2001 | Kensey et al. |
| 6,261,245 B1 | 7/2001 | Kawai et al. |
| 6,271,045 B1 | 8/2001 | Douglas et al. |
| 6,283,926 B1 | 9/2001 | Cunningham et al. |
| 6,283,982 B1 | 9/2001 | Levaughn et al. |
| 6,285,454 B1 | 9/2001 | Douglas et al. |
| 6,306,104 B1 | 10/2001 | Cunningham et al. |
| 6,306,152 B1 | 10/2001 | Verdonk et al. |
| 6,315,738 B1 | 11/2001 | Nishikawa et al. |
| 6,319,210 B1 | 11/2001 | Douglas et al. |
| 6,332,871 B1 | 12/2001 | Douglas et al. |
| 6,346,114 B1 | 2/2002 | Schraga |
| 6,352,514 B1 | 3/2002 | Douglas et al. |
| 6,364,889 B1 | 4/2002 | Kheiri et al. |
| 6,364,890 B1 | 4/2002 | Lum et al. |
| 6,375,627 B1 | 4/2002 | Mauze et al. |
| 6,379,317 B1 | 4/2002 | Kintzig et al. |
| 6,379,969 B1 | 4/2002 | Mauze et al. |
| 6,391,005 B1 | 5/2002 | Lum et al. |
| 6,402,701 B1 | 6/2002 | Kaplan et al. |
| 6,402,704 B1 | 6/2002 | McMorrow |
| 6,409,740 B1 | 6/2002 | Kuhr et al. |
| 6,419,661 B1 | 7/2002 | Kuhr et al. |
| 6,423,011 B1 | 7/2002 | Arulkumaran et al. |
| 6,455,324 B1 | 9/2002 | Douglas |
| 6,461,496 B1 | 10/2002 | Feldman et al. |
| 6,464,649 B1 | 10/2002 | Duchon et al. |
| 6,472,220 B1 | 10/2002 | Simons et al. |
| 6,485,439 B1 | 11/2002 | Roe et al. |
| 6,488,891 B2 | 12/2002 | Mason et al. |
| 6,491,709 B2 | 12/2002 | Sharma et al. |
| 6,497,845 B1 | 12/2002 | Sacherer |
| 6,503,210 B1 | 1/2003 | Hirao et al. |
| 6,506,575 B1 | 1/2003 | Knappe et al. |
| 6,530,892 B1 | 3/2003 | Kelly |
| 6,589,260 B1 | 7/2003 | Schmelzeisen-Redeker et al. |
| 6,706,000 B2 | 3/2004 | Perez et al. |
| 6,706,159 B2 | 3/2004 | Moerman et al. |
| 6,730,046 B1 | 5/2004 | Hamamoto et al. |
| 6,743,211 B1 | 6/2004 | Prausnitz et al. |
| 6,752,817 B2 | 6/2004 | Flora et al. |
| 6,808,499 B1 | 10/2004 | Churchill et al. |
| 6,837,858 B2 | 1/2005 | Cunningham et al. |
| 7,041,068 B2 | 5/2006 | Freeman et al. |
| 2001/0011157 A1 | 8/2001 | Latterell et al. |
| 2001/0027327 A1 | 10/2001 | Schraga |
| 2001/0031931 A1 | 10/2001 | Cunningham et al. |
| 2001/0039387 A1 | 11/2001 | Rutynowski et al. |
| 2001/0044615 A1 | 11/2001 | Amano et al. |
| 2002/0002344 A1 | 1/2002 | Douglas et al. |
| 2002/0004196 A1 | 1/2002 | Whitson |
| 2002/0022789 A1 | 2/2002 | Perez et al. |
| 2002/0029059 A1 | 3/2002 | Purcell |
| 2002/0040230 A1 | 4/2002 | Kuhr et al. |
| 2002/0052618 A1 | 5/2002 | Haar et al. |
| 2002/0077584 A1 | 6/2002 | Lin et al. |
| 2002/0082522 A1 | 6/2002 | Douglas et al. |
| 2002/0082543 A1 | 6/2002 | Park et al. |
| 2002/0087110 A1 | 7/2002 | Effenhauser et al. |
| 2002/0103499 A1 | 8/2002 | Perez et al. |
| 2002/0115967 A1 | 8/2002 | Svedman |
| 2002/0169470 A1 | 11/2002 | Kuhr et al. |
| 2002/0177761 A1 | 11/2002 | Orloff et al. |
| 2002/0177788 A1 | 11/2002 | Hodges et al. |
| 2003/0069509 A1 | 4/2003 | Matzinger et al. |
| 2003/0083685 A1 | 5/2003 | Freeman et al. |
| 2003/0083686 A1 | 5/2003 | Freeman et al. |
| 2003/0088191 A1 | 5/2003 | Freeman et al. |
| 2003/0093093 A1 | 5/2003 | Modesitt et al. |
| 2003/0191415 A1 | 10/2003 | Moerman et al. |
| 2003/0199789 A1 | 10/2003 | Boecker et al. |
| 2003/0199790 A1 | 10/2003 | Boecker et al. |
| 2003/0199791 A1 | 10/2003 | Boecker et al. |
| 2003/0199898 A1 | 10/2003 | Boecker et al. |
| 2003/0199899 A1 | 10/2003 | Boecker et al. |
| 2003/0199901 A1 | 10/2003 | Boecker et al. |
| 2003/0199902 A1 | 10/2003 | Boecker et al. |
| 2003/0199903 A1 | 10/2003 | Boecker et al. |
| 2003/0199909 A1 | 10/2003 | Boecker et al. |
| 2003/0199911 A1 | 10/2003 | Boecker et al. |
| 2003/0208140 A1 | 11/2003 | Pugh |
| 2003/0212424 A1 | 11/2003 | Briggs et al. |
| 2003/0233112 A1 | 12/2003 | Alden et al. |
| 2003/0233113 A1 | 12/2003 | Alden et al. |
| 2006/0178690 A1 | 8/2006 | Freeman et al. |

FOREIGN PATENT DOCUMENTS

| | | |
|---|---|---|
| DE | 35 08 365 A1 | 8/1985 |
| DE | 37 08 031 A1 | 11/1987 |
| EP | 0 212 906 A2 | 3/1987 |
| EP | 0 365 196 A1 | 4/1990 |
| EP | 0 453 283 A1 | 10/1991 |
| EP | 0 568 024 A2 | 11/1993 |
| EP | 0 622 046 A2 | 11/1994 |
| EP | 0 671 146 A1 | 9/1995 |
| EP | 0 688 532 A2 | 12/1995 |
| EP | 1 112 717 | 7/2001 |
| FR | 2 590 673 | 5/1987 |
| GB | 2 222 251 A | 2/1990 |
| JP | 02-120655 | 5/1990 |
| JP | H02-170388 A | 7/1990 |
| JP | 04-194660 | 7/1992 |
| JP | H06-004150 A | 1/1994 |
| JP | 08-000598 | 1/1996 |
| JP | 09-084781 | 3/1997 |
| JP | 09-089885 | 4/1997 |
| JP | H09-276235 | 10/1997 |
| JP | 09-294737 | 11/1997 |
| JP | 2000-116768 A | 4/2000 |
| JP | 2000-152923 A | 6/2000 |
| JP | 2001-095787 A | 4/2001 |
| WO | WO 85/04089 A1 | 9/1985 |
| WO | WO 88/00812 A1 | 2/1988 |
| WO | WO 91/06855 A1 | 5/1991 |
| WO | WO 93/02720 A1 | 2/1993 |
| WO | WO 93/09723 A1 | 5/1993 |
| WO | WO 93/12726 | 7/1993 |
| WO | WO 94/16737 A1 | 8/1994 |
| WO | WO 95/10223 A2 | 4/1995 |
| WO | WO 96/32635 A1 | 10/1996 |
| WO | WO 96/37256 A1 | 11/1996 |
| WO | WO 97/08986 A1 | 3/1997 |
| WO | WO 97/42882 A1 | 11/1997 |
| WO | WO 97/42885 A1 | 11/1997 |
| WO | WO 97/42886 A1 | 11/1997 |
| WO | WO 97/42888 A1 | 11/1997 |
| WO | WO 97/43962 A1 | 11/1997 |
| WO | WO 99/26539 A1 | 6/1999 |
| WO | WO 99/44508 | 9/1999 |
| WO | WO 99/55232 A1 | 11/1999 |
| WO | WO 00/45708 A1 | 8/2000 |
| WO | WO 01/00090 A1 | 1/2001 |
| WO | WO 01/34029 A1 | 5/2001 |
| WO | WO 01/64105 A1 | 9/2001 |
| WO | WO 01/66010 A1 | 9/2001 |
| WO | WO 01/72220 A1 | 10/2001 |
| WO | WO 01/89383 A2 | 11/2001 |

| WO | WO 02/08753 A2 | 1/2002 |
| WO | WO 02/056769 A1 | 7/2002 |
| WO | WO 03/088834 A1 | 10/2003 |
| WO | WO 03/088835 A2 | 10/2003 |

OTHER PUBLICATIONS

Brace et al., "Re-evaluation of the Needle Method for Measuring Interstitial Fluid Pressure", American Journal of Physiology, 1975, vol./Issue No. 229 (3), pp. 603-607, American Physiological Society.

DE 35 08 365 A1 English Abstract, Dec. 19, 1985.

GB 8818491A Patent Application, Aug. 3, 1988.

Ginsberg, "An Overview of Minimally Invasive Technologies", Clinical Chemistry, 1992, vol./Issue No. 38 (9), pp. 1596-1600, Becton Dickinson and Co.

Janle-Swain et al., "Use of a Capillary Filtrate Collector for Monitoring Glucose in Diabetics", ASAIO Journal, 1987, pp. 336-340, J.B. Lippincott Co.

JP 09-084781 Machine Translation, Mar. 31, 1997.

JP H09-276235 Machine Translation, Oct. 28, 1997.

Kayashima et al., "Suction Effusion Fluid from Skin and Constituent Analysis: New Candidate for Interstitial Fluid", American Journal of Physiology, 1992, vol./Issue No. 263 (5), pp. H1623-H1627, American Physiological Society.

Korthuis, R.J. et al., "Interstitium & Lymphatic Techniques", Microcirculatory Technology, 1986, pp. 317-340, Academic Press, Inc.

Turner et al., "Diabetes Mellitus: Biosensors for Research and Management", Biosensors, 1985, vol./Issue No. 1(1), pp. 85-115, Elsevier Applied Science Publishers, UK.

Wiig, Helge, "Evaluation of Methodologies for Measurement of Interstitial Fluid Pressure (Pi): Physiological Implications of Recent Pi Data", Critical Reviews in Biomedical Engineering, 1990, vol./Issue No. 18-1, pp. 27-54, CRC Press, Boca Raton, Florida.

Ash et al., "A Subcutaneous Capillary Filtrate Collector for Measurement of Blood Chemistries", ASAIO Journal, pp. M699-M705, issue/vol. 39 (3), J.B. Lippincott Co., 1992.

DE 34 26 090 A1 English Abstract, Apr. 18, 1985.

U.S. Appl. No. 10/607,347 Office Action mailed Apr. 29, 2009.

Critical Reviews in Bioengineering, 1990.

JP 2000-152923 A English Abstract.

JP 2001-095787 A English Abstract.

JP H02-170388 A English Abstract.

JP H06-004150 A English Abstract.

U.S. Appl. No. 10/165,102 Office Action mailed Oct. 5, 2007.

U.S. Appl. No. 10/607,347 Office Action mailed Sep. 2, 2009.

U.S. Appl. No. 10/753,973 Office Action mailed Dec. 26, 2008.

U.S. Appl. No. 10/753,973 Office Action mailed Jul. 28, 2009.

U.S. Appl. No. 10/835,094 Final Office Action mailed Mar. 11, 2009.

U.S. Appl. No. 11/353,849 Office Action mailed Feb. 2, 2009.

U.S. Appl. No. 10/753,973 to Duchon et al., Office Action mailed Jan. 12, 2010.

U.S. Appl. No. 11/778,331 to Douglas et al., Notice of Allowance mailed Jan. 21, 2010.

METHODS AND APPARATUS FOR SAMPLING AND ANALYZING BODY FLUID

CROSS-REFERENCE TO RELATED APPLICATIONS

This application is a divisional of application Ser. No. 10/612,852 filed Jul. 3, 2003, which is a continuation of application Ser. No. 09/887,574 filed Jun. 21, 2001, now abandoned, which is a continuation of application Ser. No. 09/552,243 filed Apr. 19, 2000, now U.S. Pat. No. 6,352,514, which is a continuation of application Ser. No. 09/298,386 filed Apr. 23, 1999, now U.S. Pat. No. 6,099,484, which is a continuation of application Ser. No. 08/858,042 filed May 16, 1997, now U.S. Pat. No. 5,951,492, which claims benefit of U.S. Provisional Application Ser. No. 60/017,133 filed May 17, 1996; U.S. Provisional Application Ser. No. 60/019,918 filed Jun. 14, 1996; U.S. Provisional Application Ser. No. 60/023,658 filed Aug. 1, 1996; U.S. Provisional Application Ser. No. 60/025,340 filed Sep. 3, 1996; U.S. Provisional Application Ser. No. 60/064,856 filed Sept. 17, 1996; U.S. Provisional Application Ser. No. 60/092,121 filed Sep. 16, 1996; and U.S. Provisional Application Ser. No. 60/044,406 filed Oct. 8, 1996, the disclosures of which are incorporated herein by reference. The present invention is related to inventions disclosed in the following concurrently filed, commonly assigned U.S. application Ser. No. 08/857,680, now U.S. Pat. No. 5,879,311 entitled "Body Fluid Sampling Device and Methods of Use"; Ser. No. 08/858,045, now U.S. Pat. No. 5,857,983 entitled "Methods and Apparatus for Sampling Body Fluid"; Ser. No. 08/858,043 entitled "Methods and Apparatus for Expressing Body Fluid From an Incision"; and Ser. No. 08/975,978 entitled "Body Fluid Sampling Device". The disclosures of those applications are incorporated herein by reference. The present invention is also related to inventions disclosed in the following, commonly assigned U.S. application Ser. No. 08/857,335 entitled "Disposable Element for Use in a Body Fluid Sampling Device," now U.S. Pat. No. 6,048,352, which is incorporated by reference.

FIELD OF THE INVENTION

The present invention relates to lancing devices and methods for obtaining samples of blood and other fluids from the body for analysis or processing.

BACKGROUND OF THE INVENTION

Many medical procedures in use today require a relatively small sample of blood, in the range of 5-50 μL. It is more cost effective and less traumatic to the patient to obtain such a sample by lancing or piercing the skin at a selected location, such as the finger, to enable the collection of 1 or 2 drops of blood, than by using a phlebotomist to draw a tube of venous blood. With the advent of home use tests such as self monitoring of blood glucose, there is a requirement for a simple procedure which can be performed in any setting by a person needing to test.

Lancets in conventional use generally have a rigid body and a sterile needle which protrudes from one end. The lancet may be used to pierce the skin, thereby enabling the collection of a blood sample from the opening created. The blood is transferred to a test device or collection device. Blood is most commonly taken from the fingertips, where the supply is generally excellent. However, the nerve density in this region causes significant pain in many patients. Sampling of alternate sites, such as earlobes and limbs, is sometimes practiced to access sites which are less sensitive. These sites are also less likely to provide excellent blood samples and make blood transfer directly to test devices difficult.

Repeated lancing in limited surface areas (such as fingertips) results in callous formation. This leads to increased difficulty in drawing blood and increased pain.

To reduce the anxiety of piercing the skin and the associated pain, many spring loaded devices have been developed. The following two patents are representative of the devices which were developed in the 1980's for use with home diagnostic test products.

U.S. Pat. No. 4,503,856, Cornell et al., describes a spring loaded lancet injector. The reusable device interfaces with a disposable lancet. The lancet holder may be latched in a retracted position. When the user contacts a release, a spring causes the lancet to pierce the skin at high speed and then retract. The speed is important to reduce the pain associated with the puncture.

Levin et al. U.S. Pat. No. 4,517,978 describes a blood sampling instrument. This device, which is also spring loaded, uses a standard disposable lancet. The design enables easy and accurate positioning against a fingertip so the impact site can be readily determined. After the lancet pierces the skin, a bounce back spring retracts the lancet to a safe position within the device.

In institutional settings, it is often desirable to collect the sample from the patient and then introduce the sample to a test device in a controlled fashion. Some blood glucose monitoring systems, for example, require that the blood sample be applied to a test device which is in contact with a test instrument. In such situations, bringing the finger of a patient directly to the test device poses some risk of contamination from blood of a previous patient. With such systems, particularly in hospital settings, it is common to lance a patient, collect a sample in a micropipette via capillary action and then deliver the sample from the pipette to the test device.

Haynes U.S. Pat. No. 4,920,977 describes a blood collection assembly with lancet and microcollection tube. This device incorporates a lancet and collection container in a single device. The lancing and collection are two separate activities, but the device is a convenient single disposable unit for situations when sample collection prior to use is desirable. Similar devices are disclosed in Sarrine U.S. Pat. No. 4,360, 016, and O'Brien U.S. Pat. No. 4,924,879.

Jordan et al. U.S. Pat. Nos. 4,850,973 and 4,858,607, disclose a combination device which may be alternatively used as a syringe-type injection device and a lancing device with disposable solid needle lancet, depending on configuration.

Lange et al. U.S. Pat. No. 5,318,584 describes a blood lancet device for withdrawing blood for diagnostic purposes. This invention uses a rotary/sliding transmission system to reduce the pain of lancing. The puncture depth is easily and precisely adjustable by the user.

Suzuki et al. U.S. Pat. No. 5,368,047, Dombrowski U.S. Pat. No. 4,653,513 and Ishibashi et al. U.S. Pat. No. 5,320,607 each describe suction-type blood samplers. These devices develop suction between the lancing site and the end of the device when the lancet holding mechanism withdraws after piercing the skin. A flexible gasket around the end of the device helps seal the end around the puncture site until adequate sample is drawn from the puncture site or the user pulls back on the device.

Garcia et al. U.S. Pat. No. 4,637,403 discloses a combination lancing and blood collection device which uses a capillary passage to conduct body fluid to a separate test strip in the form of a microporous membrane. It is necessary to achieve a precise positioning of the upper end of the capillary passage with respect to the membrane in order to ensure that body fluid from the passage is transferred to the membrane. If an appreciable gap exists therebetween, no transfer may occur.

Also, the diameter of the capillary passage is relatively small, so the width of a sample transferred to the membrane may be too small to be measured by on-site measuring devices such as an optical measuring system or an electrochemical meter.

It is difficult for a user to determine whether a sufficiently large drop of body fluid has been developed at the incision for providing a large enough sample.

International Publication Number WO 95/10223, Erickson et al., describes a means of collecting and measuring body fluids. This system uses a disposable lancing and suction device with a spacer member which compresses the skin around the lance/needle.

Single use devices have also been developed for single use tests, i.e. home cholesterol testing, and for institutional use to eliminate cross-patient contamination multi-patient use. Crossman et al. U.S. Pat. No. 4,869,249, and Swierczek U.S. Pat. No. 5,402,798, also disclose disposable, single use lancing devices.

The disclosures of the above patents are incorporated herein by reference.

An object of the present invention is to ensure that a sufficiently large drop of body fluid is developed at an incision, and that the body fluid reaches a test strip.

Another object is to ensure that the sample applied to the test strip creates a measurement area that is sufficiently wide to be properly analyzed.

An additional object is to provide a novel electrochemical analyzing system for analyzing a sample in the lancing device.

A further object is to enable a sample of body fluid to be applied to a test strip which is mounted in a lancing device.

Another object of this invention is to provide a method which can result in a sample of either blood or interstitial fluid, depending on the sample site and the penetration depth utilized. While there are no commercially available devices utilizing interstitial fluid (ISF) at this time, there are active efforts to establish the correlation of analytes, such as glucose, in ISF compared to whole blood. If ISF could be readily obtained and correlation is established, ISF may be preferable as a sample since there is no interference of red blood cells or hematocrit adjustment required.

Another object of this invention is to provide a method which can draw a small but adjustable sample, i.e. 3 μL for one test device and 8 μL for another test device, as appropriate.

Another object of this invention is to provide a method by which the drawn sample is collected and may be easily presented to a testing device, regardless of the location of the sample site on the body. This approach helps with infection control in that multiple patients are not brought in contact with a single test instrument; only the sampling device with a disposable patient-contact portion is brought to the test instrument. Alternatively, the disposable portion of a test device may be physically coupled with the sampler so the sample can be brought directly into the test device during sampling. The test device may then be read in a test instrument if appropriate or the testing system can be integrated into the sampler and the test device can provide direct results displayed for the patient.

A further object is to provide an on-site test strip with a relatively wide sample which can be analyzed by on-site analyzers such as optical and electrochemical analyzers.

It is a further object of the invention to provide a device for minimally invasive sampling comprising a reusable sampler and disposable lancet and sample collection device.

SUMMARY OF THE INVENTION

One aspect of the present invention relates to a sampling device for sampling body fluid. The device includes a housing and a lancet carrier mounted in the housing for supporting a disposable lancet. The device also includes a mechanism for displacing the lancet carrier toward a lower end of the housing for forming an incision in a user. A body fluid sampling member is mounted in the housing for conducting body fluid from the incision. That sampling member comprises a capillary member, and a test strip. The capillary member includes an elongated stem having a capillary passage extending longitudinally therethrough for conducting body fluid upwardly by capillary action. The test strip is affixed to the capillary member at an upper end thereof and in communication with the capillary passage for receiving a sample of body fluid.

Preferably, the test strip comprises a microporous membrane, and an absorbent pad is preferably disposed between the test strip and the upper end of the capillary passage for wicking body fluid from the passage to the test strip.

The present invention also relates to the capillary member per se.

Another embodiment of the sampling device includes a housing, a lancet carrier mounted in the housing for supporting a disposable lancet, a mechanism for displacing the lancet carrier toward a lower end of the housing for forming an incision in a user, and a strip-holding mechanism mounted at a lower end of the housing for supporting a test strip across the lower end of the housing to enable the test strip to pick up body fluid from the incision.

The strip holding mechanism preferably comprises a sleeve disposed in surrounding relationship to the lancet carrier and includes radially aligned slots for receiving a test strip.

Preferably, the sleeve constitutes a first sleeve, and the holding mechanism further includes a second sleeve surrounding the first sleeve and including slots that are radially aligned with the slots of the first sleeve. The second sleeve is slidable longitudinally relative to both the housing and the first sleeve and is spring biased downwardly. The slots which are formed in the second sleeve are elongated in a direction parallel to a longitudinal axis of the housing to enable the second sleeve to move longitudinally relative to a test strip mounted in the first sleeve.

The present invention also relates to a method of sampling body fluid which comprises the steps of positioning a lower end of a sampling device against a skin surface, and displacing a lancet carrier toward the lower end of the sampling device to form an incision through the skin. A test strip is positioned in the sampling device to extend across the lower end thereof. The sampling device is moved toward the incision to bring the test strip into contact with body fluid emerging from the incision. The test strip is preferably positioned in the sampling device prior to the displacement of the lancet toward the lower end of the sampling device, whereby the lancet pierces the test strip.

Another aspect of the invention involves the provision of a drop-detecting mechanism on the lancing device adjacent a lower end thereof for detecting a drop of body fluid on the user's skin. The mechanism can be in the form of electrodes which contact the drop, or an optical system including a light emitter and a light sensor. The drop-detecting mechanism automatically determines whether a drop of sufficient size has been developed at the incision for providing a proper sample.

BRIEF DESCRIPTION OF THE DRAWINGS

The objects and advantages of the invention will become apparent from the following detailed description of preferred embodiments thereof in connection with the accompanying drawings in which like numerals designate like elements and in which.

DETAILED DESCRIPTION OF PREFERRED EMBODIMENTS OF THE INVENTION

Figure 1:
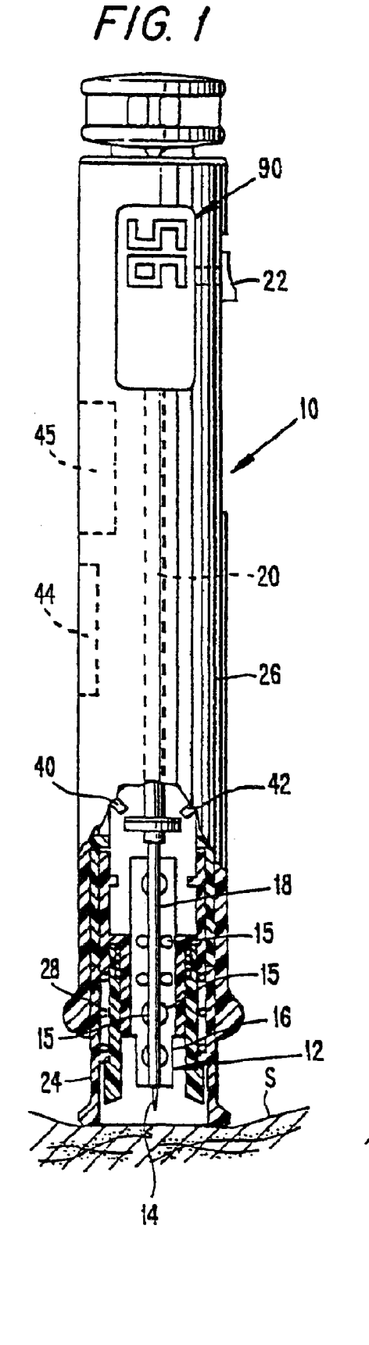
FIG. 1 is a side elevational view, partially broken away, of a blood sampling device according to the present invention, with a capillary tube thereof disposed in a retracted state.
Figures 2, 3, 4:
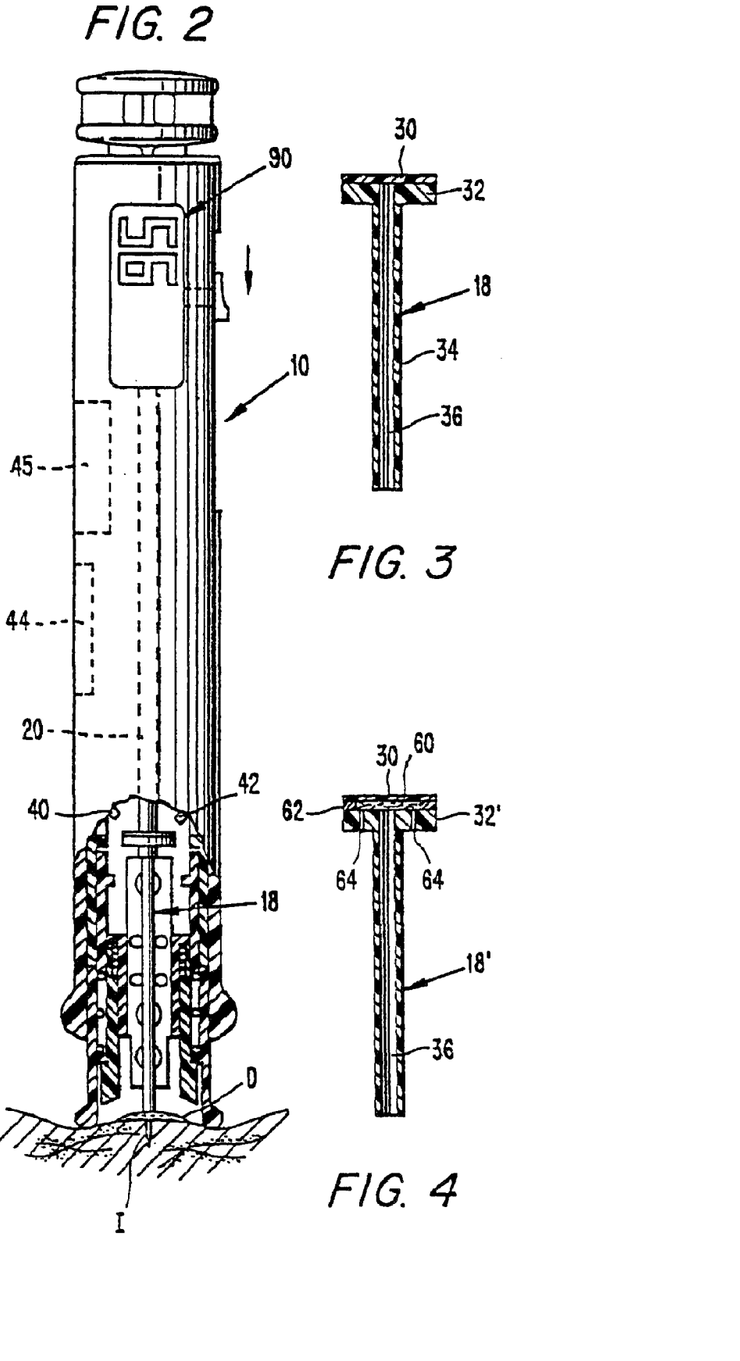
FIG. 2 is a view similar to FIG. 1 after an incision has been made, and the capillary tube has been extended.
FIG. 3 is a longitudinal sectional view through one embodiment of the capillary tube according to the present invention.
FIG. 4 is a longitudinal sectional view taken through another embodiment of a capillary tube according to the present invention.

Depicted in FIGS. 1 and 2 is a lancing device 10 for making an incision through a skin surface S, wherein a disposable lancet 12 (hereinafter referred to as a "disposable") which carries a skin-lancing member in the form of a needle 14 can be displaced toward the skin surface by a cocked spring and then rapidly retracted by another spring. Devices of this general type are known, and one preferred device is disclosed in commonly assigned, concurrently filed U.S. application Ser. No. 08/857,680, now U.S. Pat. No. 5,879,311, the disclosure of which is incorporated herein by reference.

As disclosed in that application, the disposable 12 includes a body 16 which carries not only the needle 14, but also a capillary tube 18. The capillary tube is mounted by friction fit between holding elements 15 that are integral with the body 16 and is downwardly slidable relative to the body 16 in response to manual downward displacement of a pusher 20 which possesses an exposed actuator knob 22.

The disposable 12 is situated telescopingly within a cylindrical stimulator sleeve 24 which is slidable longitudinally relative to a housing 26 of the device. The sleeve 24 is biased downwardly, or forwardly, by a spring 28. Following the cutting of an incision I in the skin and the retraction of the lancet, the housing can be repeatedly pushed downwardly against the skin as required to express the appropriate sample from the incision, whereupon the sleeve depresses a ring of body tissue in surrounding relationship to the incision, causing the incision to bulge while spreading apart the sides of the incision. Consequently, a drop D of body fluid such as blood or interstitial fluid is formed at the open end of the incision, even if the incision I has been made in a region of the body where the supply of body fluid is relatively low as compared to, say, the fingertip region.

Once the drop D has been created, the pusher 22 is displaced to push the capillary tube downwardly to a state where the lower end of the capillary tube can be dipped into the body fluid drop to obtain a sample. The pusher is then released for return to an upper position by a return spring (not shown). As disclosed in the aforementioned application, the fluid can then be transferred from the capillary tube to a test strip, thereby making the overall sampling procedure more convenient.

In accordance with the present invention, the sampling procedure is made even more convenient by eliminating the need to transfer the body fluid from the capillary tube.

In a first embodiment, the capillary tube carries its own test strip. Depicted in FIG. 3 is a test strip 30 in the form of a microporous membrane (preferably of the type disclosed in commonly assigned U.S. application Seri. No. 08/628,489, filed Apr. 5, 1996, the disclosure of which is incorporated by reference herein).

The membrane 30 is bonded, e.g. by a suitable adhesive, to an enlarged head or flange portion 32 of the capillary tube 18 which projects laterally with respect to a stem portion 34 of the capillary tube. The head 32, when viewed from the top, can be of any shape, such as circular or rectangular (e.g., square). A capillary passage 36 extends longitudinally through the stem 34 and head 32 to conduct body fluid into contact with the membrane by capillary action.

As is known in the art of capillary tubes, the amount of body fluid which is drawn up by capillary action can be regulated by a suitable selection of diameter and length of the passage 36, thereby ensuring that a proper dosing of the membrane is achieved.

Fluid analyzing instruments can be mounted within the housing. For example, a conventional optical analyzing mechanism can be provided which includes a light source 40 and a light sensor 42 such as a phototransistor, which are electrically connected to a conventional electronics unit 44 for monitoring a color change of the sample as the sample reacts with chemicals in the test strip. The electronics unit 44 displays the results on a display panel 90. In that way, for example, the glucose level in blood can be measured. The unit 44 is electrically connected to a battery 45 that is mounted in the housing.

In lieu of an optical analyzing mechanism, an electrochemical mechanism can be provided in a device 10' (FIG. 5), the mechanism including an electrochemical meter 50 which measures glucose levels. The meter 50 is electrically connected to a battery 51 mounted in the housing. The test strip 52 in this case would be provided with a printed electrical circuit, and the pusher 24' would possess electrical leads 54 positioned so as to contact respective portions of the printed circuit electrical paths on the test strip when the pusher 24' is in its lower position (after having pushed the capillary tube down). Thus, the sample conducted to the test strip 52 by the capillary tube will contact the electrical circuit for conducting a current therebetween when the leads 54 are brought into contact with the circuit. The leads are connected to the meter 50 which measures the current. Since the level of current is proportional to the glucose concentration, the meter 50 is able to measure that concentration.

When the disposable 12 is discarded after a testing operation, the capillary tube 18 and test strip 30 will be discarded therewith. A fresh disposable is then installed to present a new needle 14, capillary tube 18 and test strip 30. Thus, the user never has to touch or otherwise maneuver a test strip separately from the capillary tube, since the test strip is attached thereto.

An alternate embodiment of a capillary tube 18' is depicted in FIG. 4 wherein an absorbent pad 60 is disposed between the test strip 30 and the head 32' of the capillary tube 18'. That is, the absorbent pad, which can be formed of cellulose or suitable membrane, is bonded to the capillary tube 18', and the membrane 30 is bonded to the absorbent pad, or to a ring 62 which extends around a circumferential outer edge face of the absorbent pad 60. That ring, together with the flange 32, forms a cover which covers portions of the absorbent pad not covered by the membrane 30 to prevent the escape of the body fluid sample. When the capillary tube draws-up body fluid by capillary action, that fluid is wicked by the absorbent pad and supplied to the test strip 30. An advantage of the capillary tube 18' is that the absorbent pad will spread-out the fluid so that a wider sample is applied to the test strip to facilitate analysis.

A backpressure may occur which opposes a flow of body fluid through the absorbent pad 60. To deal with that potential problem, the head 32' is provided with air vent openings 64 to relieve the backpressure and facilitate the flow of fluid through the pad 60. The air vents are spaced laterally from the passage 36 and communicate with the pad. The diameter of the vent openings is smaller than that of the capillary tube and small enough to prevent the passage of body fluid therethrough.

Instead of being bonded directly to the absorbent pad 60, the membrane 30 could be bonded to the ring 62. In that case, the absorbent pad 60 could be bonded to the membrane, or to the cover, or to the capillary tube.

In any event it will be appreciated that the test strip is affixed, either directly or indirectly, to the capillary tube to constitute an integral part thereof.

One problem faced by a user is being able to determine whether a drop of body fluid expressed from an incision is of sufficient size to provide a proper sample. That determination can be made automatically by a sampling device 10" in accordance with an embodiment of the invention depicted in FIG. 6 wherein a drop sensing mechanism 65 is mounted on an inner sleeve 66. The drop sensing mechanism comprises a pair of diametrically opposed elements 67, 68. In one embodiment, those elements comprise a pair of electrodes connected by wires 69 to the battery 45 or 51 and positioned such that when the outer sleeve 24 is retracted in response to a pressing down of the housing, the electrodes will make contact with the drop of body fluid only if the drop is of sufficient height to provide an adequate sample. If such contact is made, the drop will close a circuit, enabling a sensor to determine that the drop is of ample size. An indicator, such as a lamp 71 can be energized to advise the user.

Figure 6:
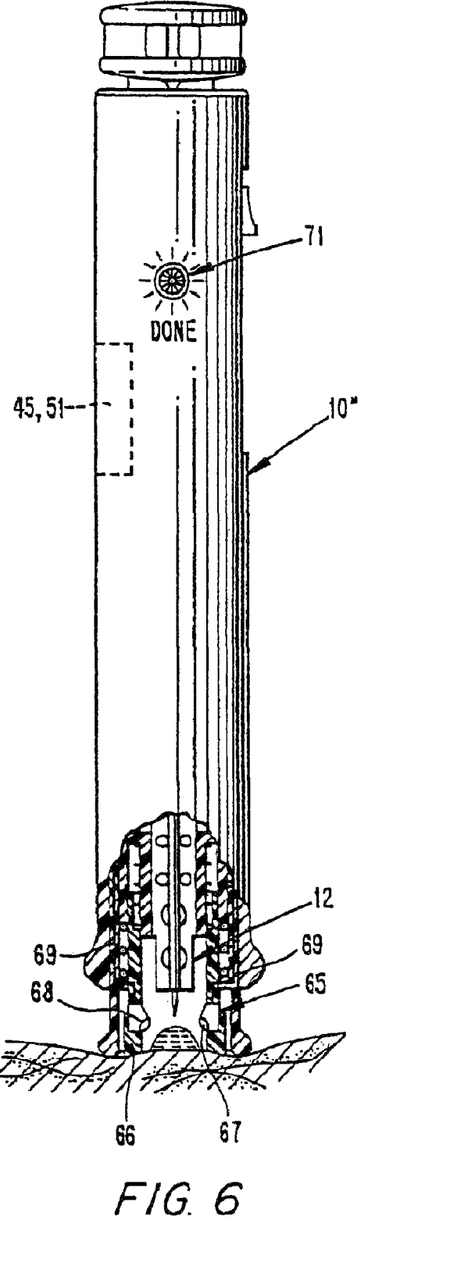
FIG. 6 is a fragmentary view of a lower end of a lancing device, depicting a drop-detecting mechanism according to the present invention.

Alternatively, the elements 67, 68 of the mechanism 65 could comprise a light emitter and light receiver, respectively. When the drop of body fluid is of sufficient height, it will block the transmission of light to the receiver, thus indicating that the drop is of sufficient size, and triggering the energization of the lamp 71.

Figure 5:
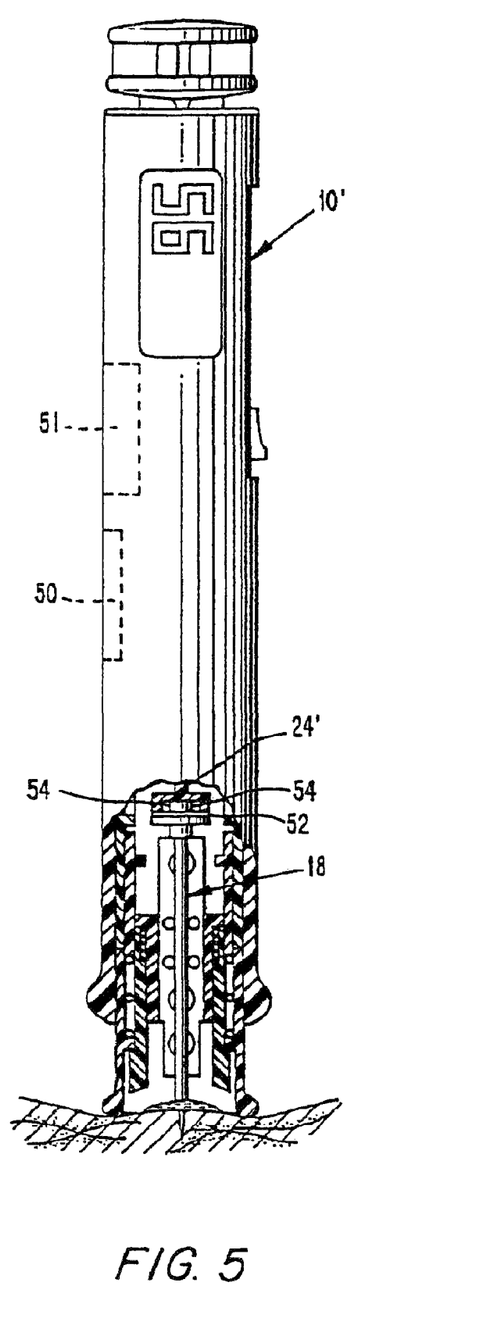
FIG. 5 is view similar to FIG. 2 of a sampling device having an alternative form of analyzing instrument.

The drop-detecting mechanism 65 can be used with either of the embodiments disclosed in connection with FIGS. 1-2 and 5. However, it is not necessary that the incision be formed by a lancet. Other incision forming devices could be used such as a laser beam or pressurized fluid. That is, known pneumatic or hydraulic injectors of the type which inject pressurized gas or liquid against the skin could be used. Such auto injectors are sold by Becton-Dickinson, for example, to inject insulin. By eliminating the insulin and merely injecting the gas (e.g., air or nitrogen) or liquid (e.g., water) at pressures above 30 psi. an incision could be formed in the skin for taking samples of body fluid. Advantageously, small particles could be mixed with the gas to promote the tissue-cutting action. The particles could comprise carbon particles of from 1 micron to 0.010 inches in diameter.

Figures 7, 8:
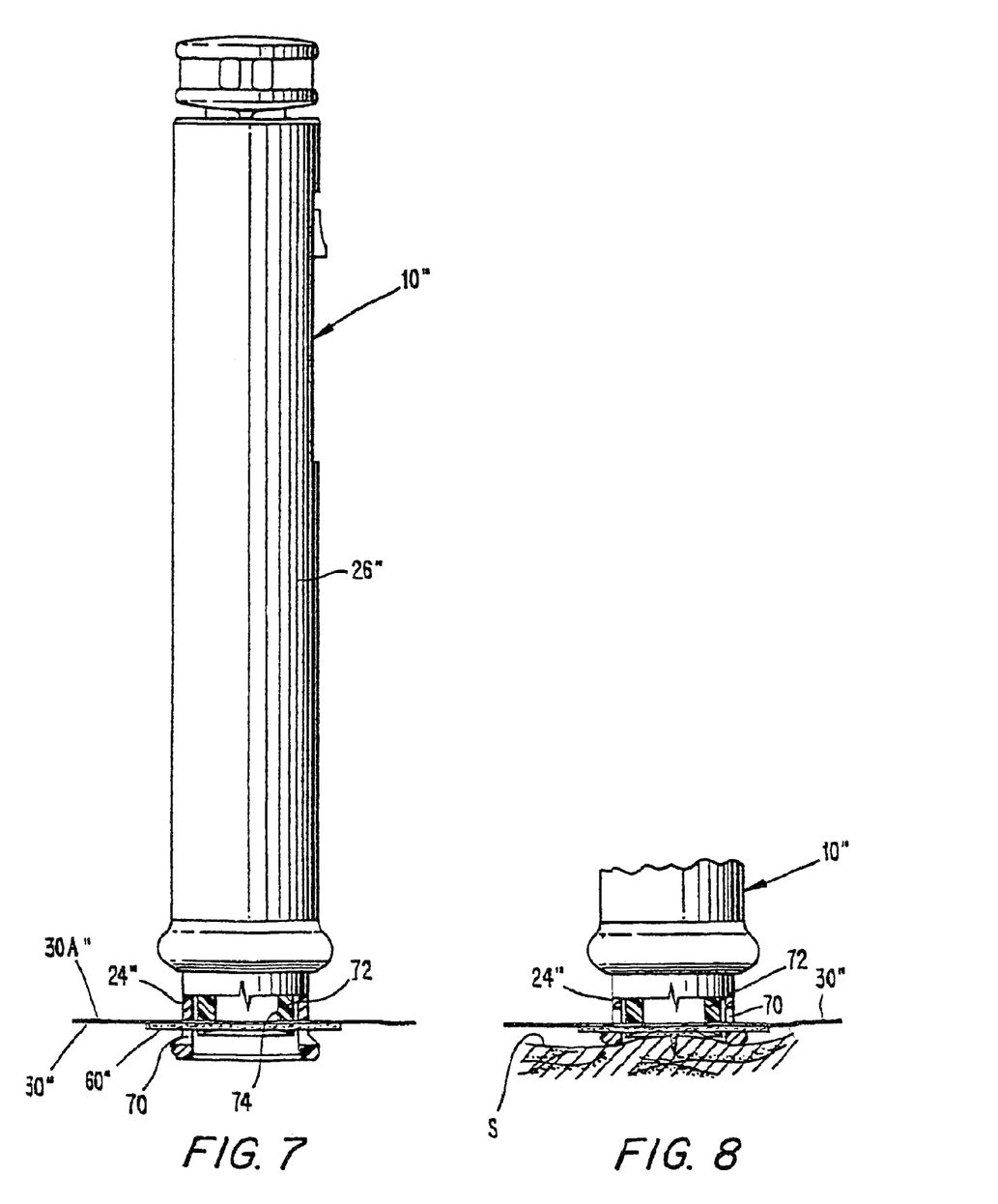
FIG. 7 is a side elevational view, partially broken away of another embodiment of the sampling device, with a test strip mounted at a lower end thereof.
FIG. 8 is a fragmentary view of the device depicted in FIG. 7 in a sampling-taking state.

Another embodiment of a sampling device 10" according to the invention is depicted in FIGS. 7 and 8. In that embodiment, the stimulator sleeve 24 is slidable longitudinally relative to housing 26" and is provided with a through-slot 70, and an inner sleeve 72 (which supports the disposable), is provided with a through-slot 74 that is aligned with the through-slot 70. Those aligned through-slots 70, 74 are adapted to receive a test strip 30" which, if desired, includes an absorbent pad 60". The test strip 30", which may comprise a porous membrane 30A" and an absorbent pad 60" attached thereto, is manually inserted through the slots 70, 74 by the user.

When a lancing procedure is performed, the lancet pierces the test strip 30" en route to the skin surface. Then, as the housing is repeatedly pushed down to pump body fluid to the open end of the incision as described earlier, the stimulator sleeve 24" will be repeatedly retracted, and simultaneously the inner sleeve 72, along with the test strip 30", will approach and contact the drop of body fluid as shown in FIG. 8, whereby a sample of the fluid is collected on the test strip.

Then, the user removes the test strip for testing at an off-site analyzer.

It will be appreciated that the present invention enables a test strip to be easily installed into and removed from a lancing device, thereby minimizing any risk of contamination of the sample. In the examples according to FIGS. 1-5 the test strip is installed along with the disposable lancet, thereby being automatically positioned in proper relationship to receive a sample and to permit the sample to be analyzed by an on-site analyzing instrument. If desired, however, the analysis could be performed by an off-site instrument by removing the disposable from the device and taking it to the off-site instrument. In the example of FIGS. 7-8, the test strip is easily installed/removed by being passed through readily accessible slots.

Although the present invention has been described in connection with preferred embodiments thereof, it will be appreciated by those skilled in the art that additions, modifications, substitutions and deletions not specifically described may be made without departing from the spirit and scope of the invention as defined in the appended claims.

What is claimed is:

1. A method of collecting a bodily fluid sample from an incision in skin comprising:

forming the incision in the skin with a needle of a bodily fluid sampling device;

pressing against the skin a stimulator sleeve of the bodily fluid sampling device around the incision to express the bodily fluid sample;

moving a capillary tube of the bodily fluid sampling device towards the incision by moving the capillary tube relative to the stimulator sleeve while the sleeve remains in contact with the skin;

drawing the bodily fluid sample from the incision into the capillary tube via capillary action;

wherein the needle and the capillary tube are distinct components;

wherein said forming the incision in the skin includes
extending the needle towards the skin to form the incision, and
retracting the needle from the incision;

wherein said moving the capillary tube of the bodily fluid sampling device towards the incision occurs after said retracting the needle from the incision;

wherein said drawing the bodily fluid sample from the incision into the capillary tube occurs after said moving the capillary tube of the bodily fluid sampling device towards the incision; and wherein said drawing the bodily fluid sample from the incision into the capillary tube includes collecting the bodily fluid sample on the surface of the skin.

2. The method of claim 1, further comprising transferring the bodily fluid onto a test strip located at one end of the capillary tube.

3. The method of claim 2, further comprising analyzing the bodily fluid with the test strip.

4. The method of claim 3, further comprising:

wherein the needle, the capillary tube and the test strip are integrated together in a first disposable;

removing the first disposable from the bodily fluid sampling device after said drawing the bodily fluid sample from the incision into the capillary tube;

disposing of the first disposable; and loading a second disposable into the bodily fluid sampling device after said removing the first disposable from the bodily fluid sampling device.

5. A method of collecting a bodily fluid sample from an incision in skin comprising:

forming the incision in the skin with a needle of a bodily fluid sampling device;

pressing against the skin a stimulator sleeve of the bodily fluid sampling device around the incision to express the bodily fluid sample; moving a capillary tube of the bodily fluid sampling device towards the incision by moving the capillary tube relative to the stimulator sleeve while the sleeve remains in contact with the skin;

drawing the bodily fluid sample from the incision into the capillary tube via capillary action;

wherein the needle and the capillary tube are distinct components;

wherein the needle and the capillary tube are integrated together in a first disposable;

removing the first disposable from the bodily fluid sampling device after said drawing the bodily fluid sample from the incision into the capillary tube;

disposing of the first disposable; and loading a second disposable into the bodily fluid sampling device after said removing the first disposable from the bodily fluid sampling device.

6. The method of claim 5, further comprising transferring the bodily fluid onto a test strip located at one end of the capillary tube.

7. The method of claim 6, further comprising analyzing the bodily fluid on the test strip.

8. The method of claim 7, wherein the analyzing the bodily fluid on the test strip includes an optical analyzing mechanism.

9. The method of claim 7, wherein the analyzing the bodily fluid on the test strip includes an electrochemical mechanism.

10. The method of claim 6, further comprising:

wherein the capillary tube includes a head and an absorbent pad; and wherein the absorbent pad is disposed between the test strip and the head of the capillary tube.

11. The method of claim 10, wherein the head defines an air vent opening to relieve pressure.

12. A method of collecting a bodily fluid sample from an incision in skin, comprising:

pressing against the skin a bodily fluid sampling device housing a first disposable that includes a skin-lancing member, chemicals for analyzing the bodily fluid sample, and a capillary passage with a capillary passage opening, wherein the skin-lancing member and the capillary passage are distinct components;

cutting the incision in the skin with the skin-lancing member of the first disposable by firing the skin-lancing member and the capillary passage of the first disposable as a single unit towards the skin;

retracting the skin-lancing member and the capillary passage of the first disposable as a single unit off the skin;

collecting via capillary action from the incision the bodily fluid sample on the surface of the skin with the capillary passage by extending the passage opening of the capillary passage past the skin-lancing member;

analyzing the bodily fluid sample with the chemicals of the first disposable;

disposing of the first disposable; and loading a second disposable into the bodily fluid sampling device after said disposing of the first disposable.

13. The method of claim 12, wherein said collecting includes venting air from the capillary passage via a vent as the bodily fluid sample fills the capillary passage.

14. The method of claim 12, wherein said analyzing the bodily fluid sample includes optical analysis.

15. The method of claim 12, wherein said analyzing the bodily fluid sample includes electrochemical analysis.

16. The method of claim 12, wherein the capillary passage is located inside a capillary tube.

17. The method of claim 12, wherein the chemicals for analyzing the bodily fluid samples. part of a test strip.

* * * * *